United States Patent
Nam et al.

(10) Patent No.: US 10,850,260 B2
(45) Date of Patent: Dec. 1, 2020

(54) SUPER ABSORBENT POLYMER AND METHOD FOR PRODUCING SAME

(71) Applicant: LG Chem, Ltd., Seoul (KR)

(72) Inventors: Hye Mi Nam, Daejeon (KR); Sang Gi Lee, Daejeon (KR); Min Ho Hwang, Daejeon (KR); Soo Jin Lee, Daejeon (KR); Chang Sun Han, Daejeon (KR)

(73) Assignee: LG Chem, Ltd.

( * ) Notice: Subject to any disclaimer, the term of this patent is extended or adjusted under 35 U.S.C. 154(b) by 29 days.

(21) Appl. No.: 16/062,778

(22) PCT Filed: Apr. 12, 2017

(86) PCT No.: PCT/KR2017/003966
§ 371 (c)(1),
(2) Date: Jun. 15, 2018

(87) PCT Pub. No.: WO2018/070622
PCT Pub. Date: Apr. 19, 2018

(65) Prior Publication Data
US 2020/0009529 A1  Jan. 9, 2020

(30) Foreign Application Priority Data
Oct. 12, 2016 (KR) .................. 10-2016-0132254

(51) Int. Cl.
| C08J 3/24 | (2006.01) |
| B01J 20/26 | (2006.01) |
| A61L 15/24 | (2006.01) |
| A61L 15/60 | (2006.01) |
| B01J 20/30 | (2006.01) |
| C08F 220/06 | (2006.01) |

(52) U.S. Cl.
CPC ............ *B01J 20/267* (2013.01); *A61L 15/24* (2013.01); *A61L 15/60* (2013.01); *B01J 20/3021* (2013.01); *B01J 20/3085* (2013.01); *C08F 220/06* (2013.01); *C08J 3/243* (2013.01); *C08J 3/245* (2013.01); *C08J 2333/02* (2013.01)

(58) Field of Classification Search
None
See application file for complete search history.

(56) References Cited

U.S. PATENT DOCUMENTS

| 5,672,633 | A | 9/1997 | Brehm et al. |
| 5,797,893 | A | 8/1998 | Wada et al. |
| 2005/0027268 | A1 | 2/2005 | Qin et al. |
| 2005/0256468 | A1 | 11/2005 | Qin et al. |
| 2007/0135785 | A1 | 6/2007 | Qin et al. |
| 2008/0234420 | A1 | 9/2008 | Smith et al. |
| 2008/0280154 | A1 | 11/2008 | Kobushi et al. |
| 2010/0072421 | A1 | 3/2010 | Kitano et al. |
| 2011/0301303 | A1 | 12/2011 | Kim et al. |
| 2015/0093575 | A1 | 4/2015 | Naumann et al. |
| 2015/0225514 | A1 | 8/2015 | Kimura et al. |
| 2016/0151531 | A1 | 6/2016 | Lee et al. |
| 2016/0354757 | A1 | 12/2016 | Lee et al. |
| 2016/0361703 | A1 | 12/2016 | Jang et al. |
| 2017/0326528 | A1 | 11/2017 | Park et al. |

FOREIGN PATENT DOCUMENTS

| CN | 1696181 A | 11/2005 |
| EP | 3269758 A1 | 1/2018 |
| JP | 4380873 B2 | 12/2009 |
| JP | 5558096 B2 | 7/2014 |
| JP | 5914677 B2 | 5/2016 |
| JP | 2016113465 A | 6/2016 |
| KR | 100336706 B1 | 5/2002 |
| KR | 20050036975 A | 4/2005 |
| KR | 20060054406 A | 5/2006 |
| KR | 20060065694 A | 6/2006 |
| KR | 20060135894 A | 12/2006 |
| KR | 20080081153 A | 9/2008 |
| KR | 20110134333 A | 12/2011 |
| KR | 20140102264 A | 8/2014 |

(Continued)

OTHER PUBLICATIONS

International Search Report for PCT/KR2017/003966 dated Aug. 11, 2017
Odian, George, "Principles of Polymerization, Second Edition", John Wiley and Sons, Inc. Copyright 1981, ISBN 0-471-05146-2, p. 203.
Schwalm, Reinhold, "UV Coatings: Basic Recent Developments and New Applications," Elsevier Science, Dec. 21, 2006, ISBN-10: 0444529799, ISBN-13: 978-0444529794, p. 115.
Extended European Search Report including Written Opinion for Application No. EP17859949.4 dated Mar. 1, 2019.

(Continued)

*Primary Examiner* — David J Buttner
(74) *Attorney, Agent, or Firm* — Lerner, David, Littenberg, Krumholz & Mentlik, LLP

(57) ABSTRACT

A super absorbent polymer and a method for producing the same are disclosed herein. In some embodiments, the super absorbent polymer includes a base polymer powder including a cross-linked polymer, and first and second surface cross-linked layers formed on the base polymer powder. The first and second surface cross-linked layers are formed by further cross-linking the cross-linked polymer in the presence of a surface crosslinking agent, wherein the first and second surface cross-linked layers each include a cross-linked structure derived from epoxy-based and non-epoxy-based surface crosslinking agents. The super absorbent polymer can exhibit excellent absorbent properties even in a swollen state and thus exhibit excellent anti-rewetting effects. Accordingly, when the super absorbent polymer is used, it is possible to provide a sanitary material such as a diaper or a sanitary napkin which can give a smooth touch feeling even after the body fluid is discharged.

4 Claims, 3 Drawing Sheets

(56) References Cited

FOREIGN PATENT DOCUMENTS

| KR | 20150016126 A | 2/2015 |
|---|---|---|
| KR | 101502310 B1 | 3/2015 |
| KR | 20160063956 A | 6/2016 |
| KR | 20160076422 A | 6/2016 |
| KR | 20160091242 A | 8/2016 |
| WO | 9526209 A1 | 10/1995 |
| WO | 2004096303 A2 | 11/2004 |
| WO | 2004096304 A1 | 11/2004 |
| WO | 2008055935 A2 | 5/2008 |

OTHER PUBLICATIONS

Frederic L. Buchholz et al: "Modern Superabsorbent Polymer Technology", Wiley-VCH, 1998.
Markus Frank: "Superabsorbents", Ullmann's Encyclopedia of Industrial Chemistry, Jan. 1, 2005, pp. 1-21, XP007914266.
Third Party Observation for Application No. PCT/KR2017/003966 dated Feb. 7, 2019.

SUPER ABSORBENT POLYMER AND METHOD FOR PRODUCING SAME

CROSS-REFERENCE TO RELATED APPLICATION(S)

The present application is a national phase entry under 35 U.S.C. § 371 of International Application No. PCT/KR2017/003966, filed on Apr. 12, 2017, which claims the benefit of Korean Patent Application No. 10-2016-0132254, filed on Oct. 12, 2016, the disclosures of which are incorporated herein by reference.

TECHNICAL FIELD

The present invention relates to an olefin polymer having remarkably improved anti-rewetting effects, and a method for producing the same.

BACKGROUND ART

Super absorbent polymer (SAP) is a synthetic polymer material capable of absorbing moisture from about 500 to about 1,000 times its own weight, and each manufacturer has denominated it as different names such as SAM (Super Absorbency Material), AGM (Absorbent Gel Material) or the like. Such super absorbent polymers started to be practically applied in sanitary products, and now they are widely used for preparation of various products, for example, hygiene products such as paper diapers for children or sanitary napkins, water retaining soil products for gardening, water stop materials for the civil engineering and construction, sheets for raising seedling, fresh-keeping agents for food distribution fields, materials for poultice or the like.

In most cases, these super absorbent polymers have been widely used in the field of hygienic materials such as diapers or sanitary napkins. For these applications, the super absorbent polymer should exhibit a high moisture absorbency, it should not release the absorbed water even in the external pressure, and additionally it should well retain the shape even in a state where the volume is expanded (swelled) by absorbing water, and thereby exhibit excellent liquid permeability.

However, it is known that it is difficult to improve both a centrifuge retention capacity (CRC), which is the physical property showing the basic absorption capacity and the water retaining capacity of the super absorbent polymer, and an absorbency under load (AUL), which shows the properties of well retaining the absorbed moisture even under the external pressure. This is because, when the overall cross-linking density of the super absorbent polymer is controlled to be low, the centrifuge retention capacity can be relatively high, but the crosslinking structure may be loose, the gel strength may be low and thus the absorbency under load may be lowered. On the contrary, when controlling the crosslink density to a high level to improve the absorbency under load, it becomes difficult for moisture to be absorbed between densely crosslinked structures, so that the basic centrifuge retention capacity may be lowered. For the reasons described above, there is a limitation in providing a super absorbent polymer having improved centrifuge retention capacity and improved absorbency under load together.

However, recently, as hygiene materials such as a diaper or a sanitary napkin become thinner, super absorbent polymers are required to have higher absorption performance. Among these, improving both a centrifuge retention capacity and an absorbency under load which are conflicting physical properties, improving a liquid permeability, and so on, have become an important task.

In addition, pressure can be applied to hygiene materials such as diapers or sanitary napkins due to the weight of the user. In particular, when a super absorbent polymer applied to sanitary materials such as diapers or sanitary napkins absorbs liquid and then pressure is applied due to the weight of the user, a rewetting phenomenon where some liquid absorbed in the super absorbent polymer again leak out can occur. Accordingly, various attempts have been made to improve the absorbency under load and the liquid permeability in order to suppress such rewetting phenomenon. However, concrete methods capable of effectively suppressing the rewetting phenomenon have not been suggested.

DETAILED DESCRIPTION OF THE INVENTION

Technical Problem

It is one object of the present invention to provide a super absorbent polymer capable of effectively suppressing the rewetting phenomenon after absorbing a liquid and thus imparting a smooth touch feeling.

It is another object of the present invention to provide a method for producing the super absorbent polymer

Technical Solution

According to an embodiment of the invention, there is provided a super absorbent polymer; comprising: a base polymer powder including a cross-linked polymer in which a water-soluble ethylenically unsaturated monomer having at least partially neutralized acidic groups is cross-linked in the presence of an internal crosslinking agent; and first and second surface cross-linked layers that are further cross-linked from the cross-linked polymer in the presence of a surface crosslinking agent and are formed on the base polymer powder, wherein the first and second surface cross-linked layers each include a cross-linked structure derived from epoxy-based and non-epoxy-based surface crosslinking agents, and having a GBP change ratio calculated by the following Formula 1 of 0.90 or less.

$$\frac{0.3\ GBP - 0.3\ AGBP}{0.3\ GBP} \qquad [\text{Formula 1}]$$

in Formula 1, 0.3 GBP is a gel bed permeability (GBP) under 0.3 psi for a physiological saline solution (0.9 wt % sodium chloride aqueous solution) of a super absorbent polymer, 0.3 AGBP is a gel bed permeability (GBP) under 0.3 psi for a physiological saline solution of a super absorbent polymer having a particle size from 300 to 600 μm after swelling and drying which is obtained by a process of adding 5 g of the super absorbent polymer to 125 g of distilled water, stirring the resultant for 1 minute, drying the swollen super absorbent polymer at 100° C. for 3 hours, and then classifying the dried polymer through a U.S. standard 30 mesh screen and a U.S. standard 50 mesh screen.

The super absorbent polymer may have a centrifuge retention capacity (CRC) for a physiological saline solution of 30 to 40 g/g. The super absorbent polymer may have an absorbency under load (AUL) under 0.9 psi for a physiological saline solution of 19 to 25 g/g. The super absorbent polymer may have a free swell gel bed permeability (GBP) for a physiological saline solution of about 50 darcy to about 100 darcy.

Meanwhile, according to one embodiment of the present invention, there is provided a method for producing a super absorbent polymer comprising the steps of: carrying out a crosslinking polymerization of a monomer mixture including a water-soluble ethylenically unsaturated monomer having at least partially neutralized acidic groups in the presence of an internal crosslinking agent to form a hydrogel polymer; drying, pulverizing and classifying the hydrogel polymer to form a base polymer powder; and subjecting the surface of the base polymer powder to a first crosslinking in the presence of an epoxy-based surface crosslinking agent and then subjecting the surface of the first cross-linked base polymer powder to a second crosslinking in the presence of a non-epoxy-based surface crosslinking agent to form a surface crosslinked layer, wherein a GBP change ratio of the super absorbent polymer calculated by the following Formula 1 is 0.90 or less.

$$\frac{0.3\ GBP - 0.3\ AGBP}{0.3\ GBP} \qquad [\text{Formula 1}]$$

in Formula 1.

0.3 GBP is a gel bed permeability (GBP) under 0.3 psi for a physiological saline solution (0.9 wt % sodium chloride aqueous solution) of a super absorbent polymer, 0.3 AGBP is a gel bed permeability (GBP) under 0.3 psi for a physiological saline solution of a super absorbent polymer having a particle size from 300 to 600 μm after swelling and drying which is obtained by a process of adding 5 g of the super absorbent polymer to 125 g of distilled water, stirring the resultant for 1 minute, drying the swollen super absorbent polymer at 100° C. for 3 hours, and then classifying the dried polymer through a U.S. standard 30 mesh screen and a U.S. standard 50 mesh screen.

In the step of forming the surface crosslinked layer, examples of the epoxy-based surface crosslinking agent may include at least one polyglycidyl ether selected from the group consisting of ethylene glycol diglycidyl ether, propylene glycol diglycidyl ether, butanediol diglycidyl ether, hexanediol diglycidyl ether, diethylene glycol diglycidyl ether, triethylene glycol diglycidyl ether, polyethylene glycol diglycidyl ether, dipropylene glycol diglycidyl ether, tripropylene glycol diglycidyl ether, polypropylene glycol diglycidyl ether, and glycerol triglycidyl ether.

Further, as the non-epoxy-based surface crosslinking agent, a polyol, a carbonate-based compound or a mixture thereof may be used. Among them, examples of the polyol may include at least one selected from the group consisting of ethylene glycol, propylene glycol, 1,4-butanediol, 1,6-hexanediol, 1,2-hexanediol, 1,3-hexanediol, 2-methyl-1,3-propanediol, 2,5-hexanediol, 2-methyl-1,3-pentanediol, 2-methyl-2,4-pentanediol, tripropylene glycol and glycerol, and examples of the carbonate-based compound may include at least one selected from the group consisting of ethylene carbonate and propylene carbonate.

In the step of forming the surface crosslinked layer, the surface of the base polymer powder may be subjected to a first surface crosslinking at a temperature of 120 to 160° C. for 5 to 40 minutes using an epoxy-based surface crosslinking agent. The surface of the first surface cross-linked powder can be subjected to a second surface crosslinking at a temperature of 170 to 210° C. for 5 to 40 minutes using a non-epoxy-based surface crosslinking agent.

Meanwhile, according to one embodiment of the present invention, there is provided a super absorbent polymer; comprising: a base polymer powder including a cross-linked polymer in which a water-soluble ethylenically unsaturated monomer having at least partially neutralized acidic groups is cross-linked in the presence of an internal crosslinking agent; and first and second surface cross-linked layers that are further cross-linked from the cross-linked polymer in the presence of a surface crosslinking agent and are formed on the base polymer powder, wherein the first and second surface cross-linked layers each include a cross-linked structure derived from surface crosslinking agents that are different from each other; and having an absorbency under load (AUL) under 0.9 psi for a physiological saline solution is 19 to 25 g/g, and a GBP change ratio calculated by the following Formula 1 is 0.90 or less.

$$\frac{0.3\ GBP - 0.3\ AGBP}{0.3\ GBP} \qquad [\text{Formula 1}]$$

in Formula 1, 0.3 GBP is a gel bed permeability (GBP) under 0.3 psi for a 0.9 wt % sodium chloride aqueous solution of a super absorbent polymer, 0.3 AGBP is a gel bed permeability (GBP) under 0.3 psi for a physiological saline solution of a super absorbent polymer having a particle size from 300 to 600 μm after swelling and drying which is obtained by a process of adding 5 g of the super absorbent polymer to 125 g of distilled water, stirring the resultant for 1 minute, drying the swollen super absorbent polymer at 100° C. for 3 hours, and then classifying the dried polymer through a U.S. standard 30 mesh screen and a U.S. standard 50 mesh screen.

Advantageous Effects

The super absorbent polymer according to one embodiment of the present invention can exhibit excellent absorbent properties even in a swollen state and thus exhibit excellent anti-rewetting effects. Accordingly, when the super absorbent polymer is used, it is possible to provide a sanitary material such as a diaper or a sanitary napkin which can give a smooth touch feeling even after the body fluid is discharged.

DETAILED DESCRIPTION OF THE EMBODIMENTS

Figure 1:
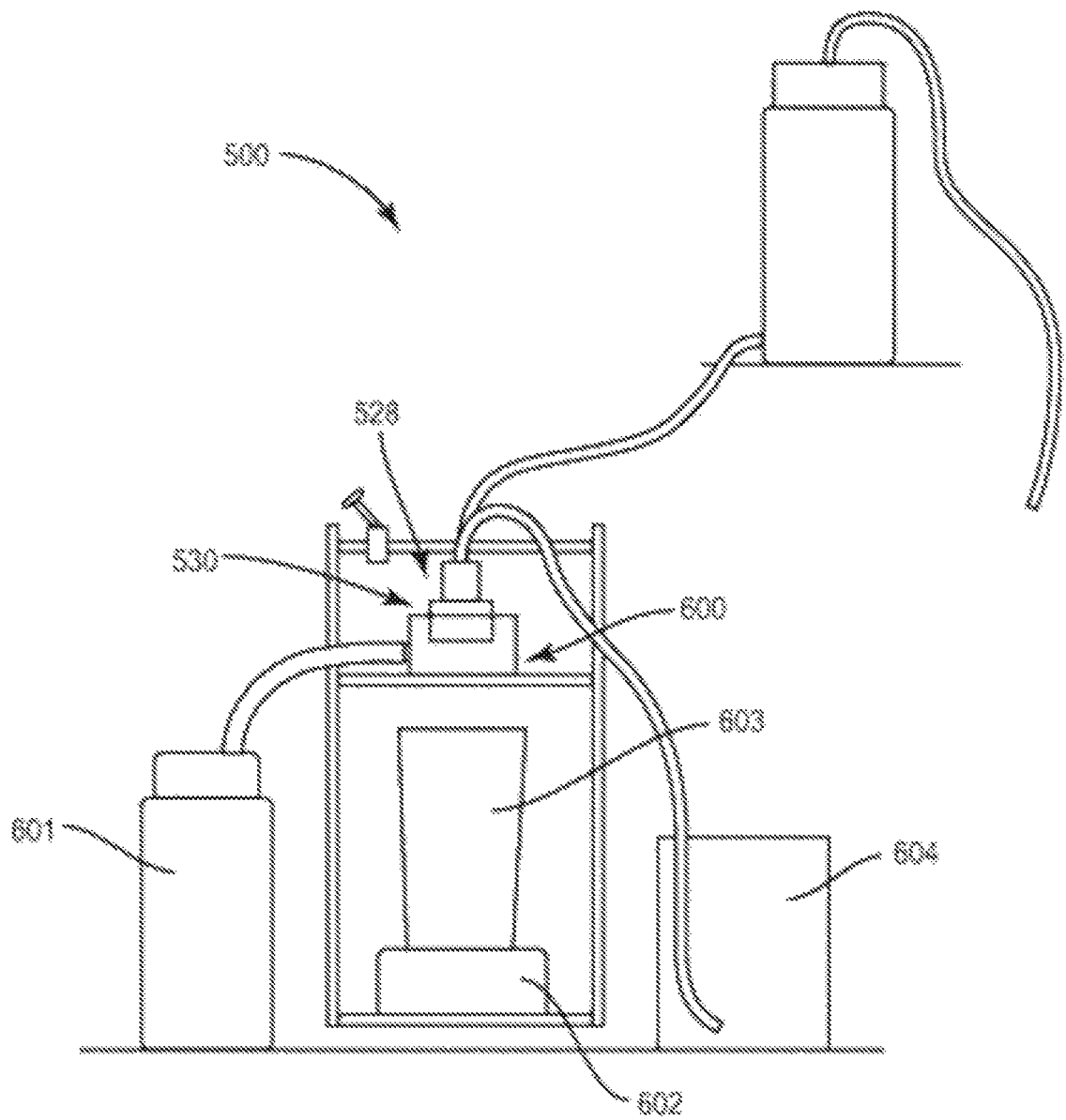
FIGS. 1 to 3 are schematic views of an exemplary apparatus for measuring the gel bed permeability and the components provided in the apparatus.

Hereinafter, a super absorbent polymer according to a specific embodiment of the present invention, a method for producing the same, and the like will be described.

According to one embodiment of the invention, there is provided a super absorbent polymer; comprising: a base polymer powder including a cross-linked polymer in which a water-soluble ethylenically unsaturated monomer having at least partially neutralized acidic groups is cross-linked in the presence of an internal crosslinking agent; and first and second surface cross-linked layers that are further cross-linked from the cross-linked polymer in the presence of a surface crosslinking agent and are formed on the base polymer powder, wherein the first and second surface cross-linked layers each include a cross-linked structure derived from epoxy-based and non-epoxy-based surface crosslinking agents, and having a GBP change ratio calculated by the following Formula 1 is 0.90 or less.

$$\frac{0.3\ GBP - 0.3\ AGBP}{0.3\ GBP} \quad \text{[Formula 1]}$$

in Formula 1, 0.3 GBP is a gel bed permeability (GBP) under 0.3 psi for a physiological saline solution (0.9 wt % sodium chloride aqueous solution) of a super absorbent polymer, 0.3 AGBP is a gel bed permeability (GBP) under 0.3 psi for a physiological saline solution of a super absorbent polymer having a particle size from 300 to 600 μm after swelling and drying which is obtained by a process of adding 5 g of the super absorbent polymer to 125 g of distilled water, stirring the resultant for 1 minute, drying the swollen super absorbent polymer at 100° C. for 3 hours, and then classifying the dried polymer through a U.S. standard 30 mesh screen and a U.S. standard 50 mesh screen.

As a result of experiments, the present inventors have found that when the super absorbent polymer is swollen, the surface cross-linking is broken and different absorbent properties from those of the super absorbent polymer before swelling is exhibited, and thus the physical properties of the swollen super absorbent polymer must be improved to improve the rewetting property of the super absorbent polymer.

In particular, a super absorbent polymer having a GBP change ratio calculated by Formula 1 of 0.90 or less can exhibit anti-rewetting effects because the absorbent properties when swollen are as good as the absorbent properties before being swollen. For more specific method of measuring a GBP change ratio change, reference may be made to Test Examples described later.

The GBP change ratio calculated by Formula 1 can be adjusted to 0.85 or less or 0.80 or less for better anti-rewetting effects. When the GBP change ratio is 0, it means that the swollen super absorbent polymer exhibits the same physical properties as the super absorbent polymer before being swollen, and thus the lower limit of the GBP change ratio can be 0.

The super absorbent polymer having a small GBP change ratio described above exhibits a high gel strength even in a swollen state, so that it can exhibit well-balanced properties of a centrifuge retention capacity, an absorbency under load and a liquid permeability.

For example, the super absorbent polymer may have a centrifuge retention capacity (CRC) for a physiological saline solution of 30 g/g to 40 g/g, 30 g/g to 35 g/g or 30 g/g to 33 g/g. The super absorbent polymer may have an absorbency under load (AUL) under 0.9 psi for a physiological saline solution of 19 to 25 g/g, 19 g/g to 23 g/g or 19 g/g to 21 g/g. The super absorbent polymer may have a free swell gel bed permeability (GBP) for a physiological saline solution of 50 to 100 darcy, 50 to 80 darcy or 55 to 70 darcy.

The super absorbent polymer can exhibit the above-mentioned CRC, AUL and GBP simultaneously. The super absorbent polymer exhibiting such balanced absorption properties can rapidly absorb a large amount of salt water at a high rate and then exhibit excellent liquid permeability while well-retaining the absorbed salt water even under the external pressure.

Consequently, the super absorbent polymer can exhibit excellent gel strength even in the swollen state. Therefore, the super absorbent polymer can effectively prevent the re-wetting phenomenon in which the absorbed saline water leaks out again even when the pressure is applied, thereby providing a sanitary material such as a diaper or sanitary napkin capable of imparting smooth touch feeling even after the body fluids are discharged.

On the other hand, in the present specification, psi is mainly used in units of pressure. Since 1 psi is 6,894.73326 Pa (N/m$^2$), the pressure input in psi can be understood by converting it to Pa which is SI unit.

The centrifuge retention capacity (CRC) for a physiological saline solution can be measured according to EDANA recommended test method No. WSP 241.2. More specifically, the centrifuge retention capacity can be obtained in accordance with the following Calculation Formula 1, after classifying super absorbent polymers to prepare a super absorbent polymer having a particle diameter of 150 μm to 850 μm, and absorbing the same in physiological saline solution for 30 minutes:

$$\text{CRC (g/g)} = \{[W_2\ (g) - W_1\ (g)]/W_0\ (g)\} - 1 \quad \text{[Calculation Formula 1]}$$

in Calculation Formula 1, $W_0$ (g) is an initial weight (g) of the super absorbent polymer having a particle diameter of 150 to 850 μm, $W_1$ (g) is a weight of a nonwoven fabric-made empty bag not containing the super absorbent polymer, measured after immersing the nonwoven fabric-made empty bag in a 0.9 wt % aqueous sodium chloride aqueous solution (physiological saline solution) for 30 minutes and then dehydrating the same by using a centrifuge at 250 G for 3 minutes, and $W_2$ (g) is a weight of the nonwoven fabric-made bag including a super absorbent polymer, measured after soaking and absorbing the super absorbent polymer having the particle diameter of 150 μm to 850 μm in a physiological saline solution at room temperature for 30 minutes, and then dehydrating the same by using a centrifuge at 250 G for 3 minutes.

In addition, the absorbency under load (AUL) at 0.9 psi can be measured according to EDANA recommended test method No. WSP 242.2. More specifically, the absorbency under load can be calculated in accordance with the following Calculation Equation 2, after absorbing the super absorbent polymer in a physiological saline solution under a load of about 0.9 psi over 1 hour:

$$\text{AUL (g/g)} = [W_4\ (g) - W_3\ (g)]/W_0\ (g) \quad \text{[Calculation Formula 2]}$$

in Calculation Equation 2.

$W_0$ (g) is an initial weight (g) of the super absorbent polymer, $W_3$ (g) is the total sum of a weight of the super absorbent polymer and a weight of the device capable of providing a load to the super absorbent polymer, and $W_4$ (g) is the total sum of a weight of the super absorbent polymer and a weight of the device capable of providing a load to the super absorbent polymer, after absorbing a physiological saline solution to the super absorbent polymer under a load (0.9 psi) for 1 hour.

$W_0$ (g) described in Calculation Equations 1 and 2 corresponds to an initial weight (g) of the super absorbent polymer, before absorbing a physiological saline solution to the super absorbent polymer, and they may be the same or different from each other.

The gel bed permeability (GBP) for a physiological saline solution was measured in units of Darcy or cm² according to the following method described in Korean Patent Application No. 10-2014-7018005. One Darcy means that it permits a flow of 1 mm/s of a fluid with viscosity of 1 cP under a pressure gradient of 1 atm/cm acting across an area of 1 cm². Gel bed permeability has the same unit as area, and 1 darcy is the same as $0.98692 \times 1012$ m² or $0.98692 \times 10^{-8}$ cm².

More specifically, as used herein. GBP means a penetration (or permeability) of a swollen gel layer (or bed) under conditions referred to as 0 psi free swell state (a Gel Bed Permeability (GBP) Under 0 psi Swell Pressure Test). 0.3 GBP means a penetration of the swollen gel layer under a load of 0.3 psi, and 0.3 AGBP means penetration of the swollen gel layer under a load of 0.3 psi for the dried super absorbent polymer after swelling. The GBP can be measured using the apparatus shown in FIGS. 1 to 3. 0.3 GBP and 0.3 AGBP can be measured by using a method of measuring the above GBP except for applying a load of 0.3 psi during swelling of the super absorbent polymer.

Figure 2:
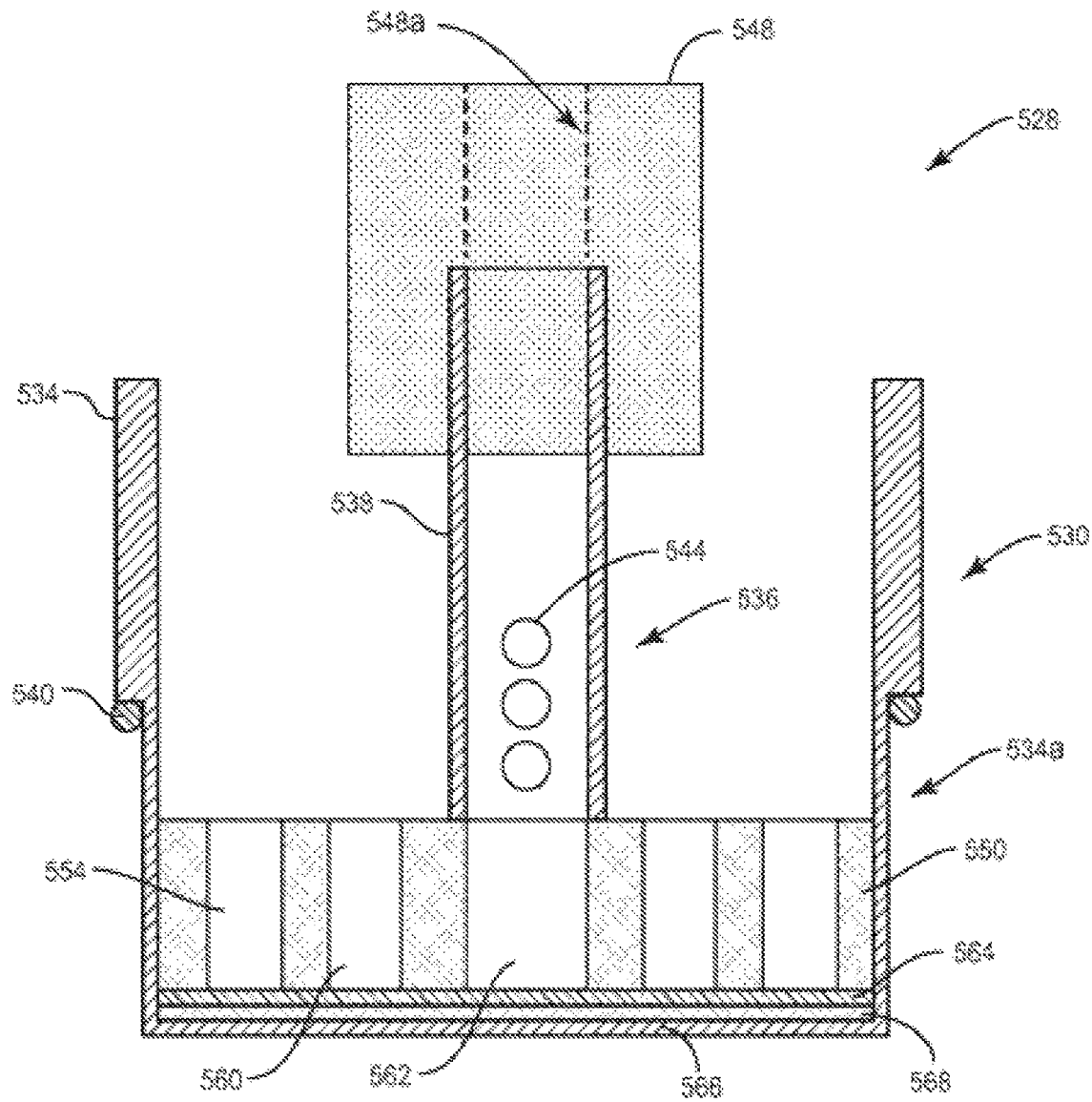
Figure 3:
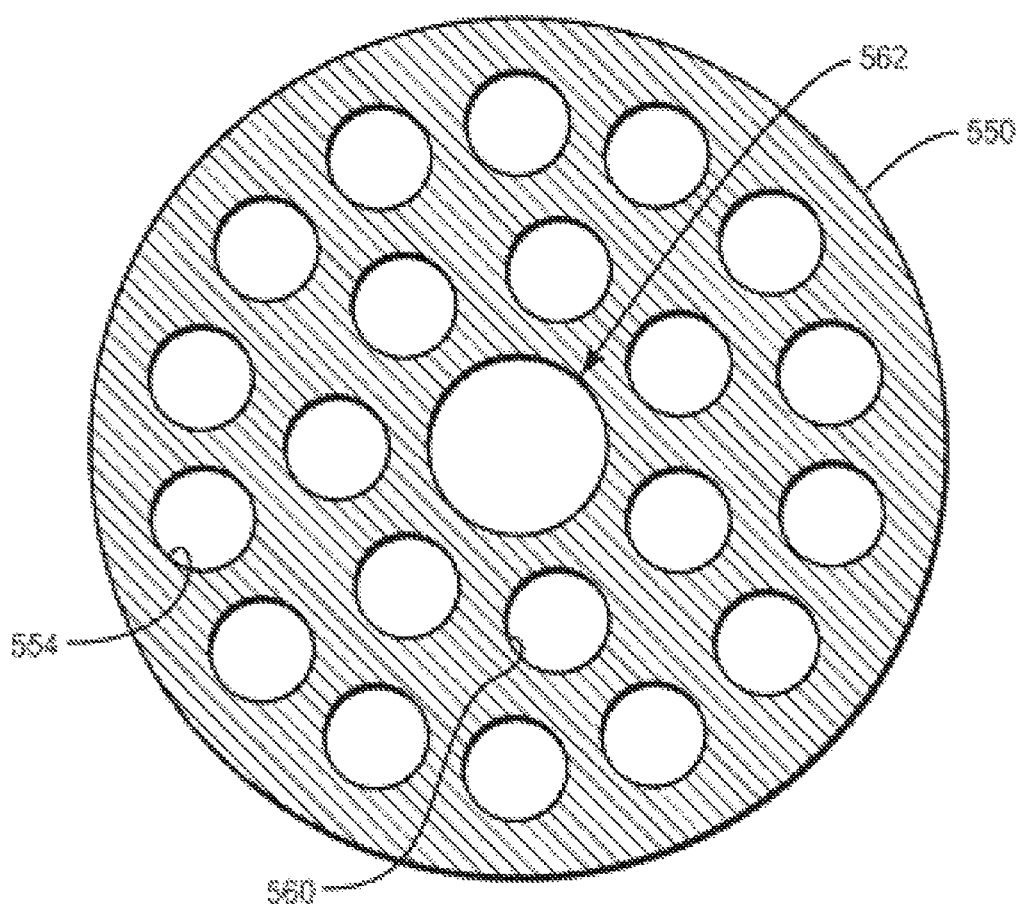

Specifically, referring to FIGS. 1-3, the test apparatus assembly 528 in a device 500 for measuring GBP includes a sample container 530 and a plunger 536. The plunger includes a shaft 538 having a cylinder hole bored down the longitudinal axis and a head 550 positioned at the bottom of the shaft. The shaft hole 562 has a diameter of about 16 mm. The plunger head is attached to the shaft, for example, by an adhesive. Twelve holes 544 are bored into the radial axis of the shaft, and three holes positioned at every 90 degrees has a diameter of about 6.4 mm. The shaft 538 is machined from a LEXAN rod or equivalent material, and has an outer diameter of about 2.2 cm and an inner diameter of about 16 mm. The plunger head 550 has seven inner holes 560 and fourteen outer holes 554, all holes having a diameter of about 8.8 mm. Further, a hole of about 16 mm is aligned with the shaft. The plunger head 550 is machined from a LEXAN rod or equivalent material and has a height of about 16 mm and a diameter sized such that it fits within the cylinder 534 with minimum wall clearance but still moves freely. The total length of the plunger head 550 and shaft 538 is about 8.25 cm, but can be machined at the top of the shaft to obtain the desired size of the plunger 536. The plunger 536 includes a 100 mesh stainless steel cloth screen 564 that is biaxially stretched to tautness and attached to the lower end of the plunger 536. The screen is attached to the plunger head 550 using a suitable solvent that causes the screen to be securely adhered to the plunger head 550. Care should be taken to avoid excess solvent moving into the openings of the screen and reducing the open area for liquid flow area. Acrylic solvent Weld-on 4 from IPS Corporation (having a place of business in Gardena, Calif., USA) can be used appropriately. The sample container 530 includes a cylinder 534 and a 400 mesh stainless steel cloth screen 566 that is biaxially stretched to tautness and attached to the lower end of the plunger 534. The screen is attached to the cylinder using a suitable solvent that causes the screen to be securely adhered to the cylinder. Care should be taken to avoid excess solvent moving into the openings of the screen and reducing the open area for liquid flow. Acrylic solvent Weld-on 4 from IPS Corporation (having a place of business in Gardena, Calif., USA) can be used appropriately. The gel particle sample (swollen super absorbent polymer), indicated as 568 in FIG. 2, is supported on the screen 566 within the cylinder 534 during testing.

Cylinder 534 may be bored from a transparent LEXAN rod or equivalent material, or it may be cut from LEXAN tubing or equivalent material, and has an inner diameter of about 6 cm (for example, a cross sectional area of about 28.27 cm²), a wall thickness of about 0.5 cm and a height of about 7.95 cm. A step can be formed by machining into the outer diameter of the cylinder 534 such that a region 534a having an outer diameter of 66 mm is present at the bottom 31 mm of the cylinder 534. An O-ring 540 which fits the diameter of the region 534a may be placed on top of the step.

The annular weight 548 has a counter-bored hole of about 2.2 cm in diameter and 1.3 cm deep so it slides freely onto the shaft 538. The annular weight also has a thru-bore 548a of about 16 mm. The annular weight 548 may be made from stainless steel or from other suitable material capable of corrosion resistance in a physiological saline solution (0.9 wt % aqueous sodium chloride solution). The combined weight of the plunger 536 and the annular weight 548 is equal to about 596 g, which corresponds to a pressure applied to the sample 568 of about 0.3 psi or about 20.7 dyne/cm² (2.07 kPa), over a sample area of about 28.27 cm².

When the test solution flows through the test apparatus during testing of the GBP, the sample container 530 generally rests on a weir 600. The purpose of the weir is to divert liquid that overflows the top of the sample container 530, and diverts the overflow liquid to a separate collection device 601. The weir can be positioned above a scale 602 with a beaker 603 resting on it to collect a physiological saline solution passing through the swollen sample 568.

In order to perform the gel bed permeability test under "free swell" conditions, the sample is swollen under no pressure in the manner described in the following (i), and in order to perform the gel bed permeability test under the condition of "pressure of 0.3 psi", the sample is swollen under pressure of 0.3 psi in the manner described in the following (ii).

(i) The plunger 536 installed with the weight 548 is placed in an empty sample container 530, and the height from the top of the weight 548 to the bottom of the sample container 530 is measured to an accuracy of 0.01 mm using an appropriate gauge. The force to which the thickness gauge applies during the measurement should be as low as possible, preferably less than about 0.74 N. When using multiple test apparatus, it is important to keep each empty sample container 530, plunger 536 and weight 548 and track of which they are used.

Further, it is preferable that the base on which the sample container 530 is placed is flat, and the surface of the weight 548 is parallel to the bottom surface of the sample container 530. Then, a sample to be tested is prepared from the super absorbent polymer for measuring GBP. As an example, a test sample is prepared from a super absorbent polymer having a particle diameter of about 300 to about 600 μm, which is passed through a US standard 30 mesh screen and retained on a US standard 50 mesh screen. About 2.0 g of a sample is placed in a sample container 530 and spread out evenly on the bottom of the sample container. The container containing 2.0 g of sample, without the plunger 536 and the weight 548 therein, is then submerged in the physiological saline solution for about 60 minutes and allow the sample to swell under no load condition.

(ii) The plunger 536 installed with the weight 548 is placed in an empty sample container 530, and the height from the top of the weight 548 to the bottom of the sample container 530 is measured to an accuracy of 0.01 mm using an appropriate gauge. The force to which the thickness gauge applies during the measurement should be as low as possible, preferably less than about 0.74 N. When using multiple test apparatus, it is important to keep each empty sample container 530, plunger 536 and weight 548 and track of which they are used.

Further, it is preferable that the base on which the sample container 530 is placed is flat, and the surface of the weight 548 is parallel to the bottom surface of the sample container 530. Then, a sample to be tested is prepared from the super absorbent polymer for measuring GBP. As an example, a test sample is prepared from a super absorbent polymer having a particle diameter of about 300 to about 600 µm, which is passed through a US standard 30 mesh screen and retained on a US standard 50 mesh screen. About 2.0 g of a sample is placed in a sample container 530 and spread out evenly on the bottom of the sample container. Then, the assembly of plunger 536 and weight 548 is placed on a sample in the sample container, and the sample container is then submerged in the physiological saline solution for about 60 minutes and allow the sample to swell under load of 0.3 psi.

In both cases (i) and (ii), the sample container 530 is placed on the mesh located in a liquid reservoir so that the sample container 530 is raised slightly above the bottom of the liquid reservoir. As the mesh, those which do not affect the movement of the physiological saline solution into the sample container 530 can be used. As such mesh, part number 7308 from Eagle Supply and Plastic (having a place of business in Appleton, Wis., USA) can be used. During saturation, the height of the physiological saline solution can be adjusted such that the surface within the sample container is defined by the sample, rather than the physiological saline solution.

At the end of this period, if the sample is swollen in the manner described in (i) above, the assembly of the plunger 536 and weight 548 is placed on the saturated sample 568 in the sample container 530 and then the sample container 530, plunger 536, weight 548 and sample 568 are removed from the solution. Meanwhile, if the sample is swollen in the manner described in (ii) above, the sample container 530, plunger 536, weight 548 and sample 568 are removed from the solution.

Thereafter, before GBP measurement, the sample container 530, plunger 536, weight 548 and sample 568 are placed on a flat, large grid non-deformable plate of uniform thickness for about 30 seconds. The plate will prevent liquid in the sample container from being released onto a flat surface due to surface tension. The plate has an overall dimension of 7.6 cm×7.6 cm, and each grid has a dimension of 1.59 cm long×1.59 cm wide×1.12 cm deep. A suitable plate material is a parabolic diffuser panel, catalogue number 1624K27, available from McMaster Carr Supply Company (having a place of business in Chicago, Ill., USA), which can then be cut to the proper dimensions.

Then, if the zero point has not changed from the initial height measurement, the height from the top of the weight 548 to the bottom of the sample container 530 is measured again by using the same thickness gauge as previously used. The height measurement should be made as soon as practicable after the thickness gauge is installed. The height measurement of the empty assembly where the plunger 536 and weight 548 are located in the empty sample container 530 should be subtracted from the height measurement obtained after saturating the sample 568. The resulting value is the thickness, or height "H" of the saturated sample 568. Further, if a plate is contained in the assembly containing the saturated sample 568, the height including the plate should be measured even when measuring the height of the empty assembly.

The GBP measurement is started by delivering a flow of a physiological saline solution into the sample container 530 containing the saturated sample 568, the plunger 536 and the weight 548. The flow rate of physiological saline solution into the container is adjusted to cause physiological saline solution to overflow the top of the cylinder 534, thereby resulting in a consistent head pressure equal to the height of the sample container 530. The physiological saline solution may be added by any suitable means that is sufficient to ensure a small, but consistent amount of overflow from the top of the cylinder, such as with a metering pump 604. The overflow liquid is diverted into a separate collection device 601. The quantity of solution passing through the sample 568 versus time is measured gravimetrically using the scale 602 and beaker 603. Data points from the scale 602 are collected every second for at least sixty seconds once the overflow has started. Data collection may be taken manually or with data collection software. The flow rate (Q) passing through the swollen sample 568 is determined in units of grams/second (g/s) by a linear least-square fit of fluid passing through the sample 568 (in grams) versus time (in seconds).

Using the data thus obtained, the gel bed permeability can be confirmed by calculating the GBP (cm$^2$) according to the following Calculation Equation 3.

$$K=[Q*H*\mu]/[A*\rho*P] \quad \text{[Calculation Equation 3]}$$

in Calculation Equation 3,
K is a gel bed permeability (cm$^2$),
Q is a flow rate (g/sec)
H is a height of swollen sample (cm),
µ is a liquid viscosity (poise) (about one cP for the test solution used with this Test),
A is a cross-sectional area for liquid flow (28.27 cm$^2$ for the sample container used with this Test),
ρ is a liquid density (g/cm$^2$)(about one g/cm$^2$, for the test solution used with this Test), and
P is a hydrostatic pressure (dyne/cm$^2$) (normally about 7,797 dynes/cm$^2$).

The hydrostatic pressure is calculated from the equation P=ρ*g*h, where ρ is a liquid density (g/cm$^2$), g is a gravitational acceleration (nominally 981 cm/sec$^2$), and h is a fluid height (for example, 7.95 cm for the GBP Test described herein).

Meanwhile, according to another embodiment of the present invention, there is provided a method for producing a super absorbent polymer having a GBP change ratio calculated by Formula 1 of 0.90 or less.

Specifically, the method for producing a super absorbent polymer comprises the steps of: carrying out a crosslinking polymerization of a monomer mixture including a water-soluble ethylenically unsaturated monomer having at least partially neutralized acidic groups in the presence of an internal crosslinking agent to form a hydrogel polymer; drying, pulverizing and classifying the hydrogel polymer to form a base polymer powder; and subjecting the surface of the base polymer powder to a first crosslinking in the presence of an epoxy-based surface crosslinking agent and then subjecting the surface of the first cross-linked base polymer powder to a second crosslinking in the presence of a non-epoxy-based surface crosslinking agent to form a surface crosslinked layer.

The water-soluble ethylenically unsaturated monomer may include at least one selected from the group consisting of anionic monomers such as (meth)acrylic acid, maleic acid, maleic anhydride, fumaric acid, crotonic acid, itaconic acid, sorbic acid, vinylphosphonic acid, vinylsulfonic acid, allylsulfonic acid, 2-(meth)acryloylethanesulfonic acid, 2-(meth)acryloyloxyethanesulfonic acid, 2-(meth)acryloylpropanesulfonic acid or 2-(meth)acrylamido-2-methylpropanesulfonic acid, and their salts; non-ionic, hydrophilic group-containing monomers of (meth)acrylamide. N-substituted (meth)acrylamide, 2-hydroxyethyl(meth)acrylate, 2-hydroxypropyl(meth)acrylate, methoxypolyethylene glycol(meth)acrylate or polyethylene glycol (meth)acrylate; and amino group-containing unsaturated monomers of (N,N)-dimethylaminoethyl(meth)acrylate or (N,N)-dimethylaminopropyl(meth)acrylamide, and their quaternary product.

In particular, the water-soluble ethylenically unsaturated monomer may be composed of a monomer (a salt of an anionic monomer) in which at least a part thereof is neutralized with an acidic group contained in the anionic monomer.

More specifically, acrylic acid or a salt thereof can be used as the water-soluble ethylenically unsaturated monomer, and in the case where acrylic acid is used, it can be used after neutralizing at least a part thereof. By using such monomer, it becomes possible to prepare a super absorbent polymer having more excellent physical properties. For example, when an alkali metal salt of acrylic acid is used as the water-soluble ethylenically unsaturated monomer, acrylic acid may be used by neutralizing it with a neutralizing agent such as sodium hydroxide (NaOH). At this time, the degree of neutralization of the acrylic acid can be adjusted to about 50 to 95 mol %, or about 60 to 85 mol %. Within this range, it is possible to provide a super absorbent polymer having excellent centrifuge retention capacity without fear of precipitation during neutralization.

In the monomer mixture containing the water-soluble ethylenically unsaturated monomer, the concentration of the water-soluble ethylenically unsaturated monomer may be about 20% to about 60% by weight, or about 25% to about 50% by weight based on the total amount of the monomer mixture including respective raw materials, polymerization initiator, solvent and the like described below, which may be appropriately adjusted in consideration of polymerization time, the reaction conditions and the like. However, if the concentration of the monomer is excessively low, the yield of the super absorbent polymer can be lowered and thus economic problems may arise. On the other hand, if the concentration is excessively high, it may arise problems in the processes, for example, a part of the monomer may be precipitated, or the pulverization efficiency may be lowered during pulverization of the polymerized hydrogel polymer, etc., and the physical properties of the super absorbent polymer may be deteriorated.

The internal crosslinking agent is included in the monomer mixture in order to carry out a cross-linking polymerization of the water-soluble ethylenically unsaturated monomer. The internal crosslinking agent is composed of a compound containing two or more crosslinkable functional groups in the molecule. The internal crosslinking agent may include a carbon-carbon double bond in the crosslinkable functional group for smooth cross-linking polymerization reaction of the above-mentioned water-soluble ethylenically unsaturated monomer. More specific examples of these internal crosslinking agents include at least one selected from the group consisting of polyethylene glycol diacrylate (PEGDA), glycerine diacrylate, glycerin triacrylate, unmodified or ethoxylated trimethylolpropane triacrylate (TMPTA), hexanediol diacrylate, and triethylene glycol diacrylate.

The internal crosslinking agent can be contained at a concentration of about 0.01 to about 5% by weight with respect to the monomer mixture, thereby forming a cross-linked polymer exhibiting high absorption rate while having excellent centrifuge retention capacity and absorbency under load.

In addition, the monomer mixture may further include a polymerization initiator that is generally used in the production of a super absorbent polymer.

Specifically, the polymerization initiator can be appropriately selected depending on the polymerization method. When a thermal polymerization method is carried out, a thermal polymerization initiator is used. When a photo-polymerization method is carried out, a photo-polymerization initiator is used. When a hybrid polymerization method (a method using both thermal and photo) is used, both a thermal polymerization initiator and a photo-polymerization initiator can be used. However, even in the case of the photo-polymerization method, a certain amount of heat is generated by light irradiation such as ultraviolet irradiation or the like, and a certain amount of heat is generated in accordance with the progress of the polymerization reaction, which is an exothermic reaction, and thus, a thermal polymerization initiator may be further used.

The photo-polymerization initiator that can be used is not particularly limited by its constitution as long as it is a compound capable of forming a radical by light such as ultraviolet rays.

The photo-polymerization initiator used herein may include, for example, at least one selected from the group consisting of benzoin ether, dialkyl acetophenone, hydroxyl alkylketone, phenyl glyoxylate, benzyl dimethyl ketal, acyl phosphine and α-aminoketone. Meanwhile, specific examples of the acylphosphine include diphenyl(2,4,6-trimethylbenzoyl)phosphine oxide, phenylbis(2,4,6-trimethylbenzoyl)phosphine oxide, ethyl(2,4,6-trimethylbenzoyl) phenylphosphinate, and the like. More various photo-polymerization initiators are well disclosed in "UV Coatings: Basics, Recent Developments and New Application" written by Reinhold Schwalm, (Elsevier, 2007), p 115, the content of which is incorporated herein by reference.

The photo-polymerization initiator may be included in a concentration of about 0.0001 to about 2.0% by weight with respect to the monomer mixture. When the concentration of the photo-polymerization initiator is too low, the polymerization rate may become slow, and when the concentration of the photo-polymerization initiator is too high, the molecular weight of the super absorbent polymer may be small and the physical properties may become uneven.

Further, as the thermal polymerization initiator, at least one selected from the group consisting of persulfate-based initiator, azo-based initiator, hydrogen peroxide and ascorbic acid can be used. Specifically, examples of the persulfate-based initiators include sodium persulfate ($Na_2S_2O_8$), potassium persulfate ($K_2S_2O_8$), ammonium persulfate (($NH_4$)$_2S_2O_8$) and the like, and examples of the azo-based initiator include 2,2-azobis(2-amidinopropane)dihydrochloride, 2,2-azobis-(N,N-dimethylene)isobutyramidine dihydrochloride, 2-(carbamoylazo)isobutylonitril, 2,2-azobis[2-(2-imidazolin-2-yl)propane]dihydrochloride, 4,4-azobis-(4-cyanovaleric acid) and the like. More various thermal polymerization initiators are well disclosed in "Principle of Polymerization" written by Odian, (Wiley, 1981), p 203, the content of which is incorporated herein by reference.

The thermal polymerization initiator may be included at a concentration of about 0.001 to about 2.0% by weight with respect to the monomer mixture. If the concentration of such a thermal polymerization initiator is too low, additional thermal polymerization hardly occurs and the effect due to the addition of the thermal polymerization initiator may be insignificant. If the concentration of the thermal polymerization initiator is excessively high, the molecular weight of the super absorbent polymer may be small and the physical properties may become uneven.

The monomer mixture may further include a foaming agent in order to produce the super absorbent polymer having a porous structure. As such foaming agent, carbonate can be used. As the carbonate, at least one selected from the group consisting of magnesium carbonate, calcium carbonate, sodium bicarbonate, sodium carbonate, potassium bicarbonate and potassium carbonate can be used.

The foaming agent may be used in an amount ranging from about 0.1% to about 0.3% by weight based on the total weight of the monomer mixture, and thus a polymer exhibiting a gel strength while having a porous structure can be provided.

In addition, the monomer mixture may further include a surfactant in order to induce a stable bubble generation. As such a surfactant, at least one surfactant selected among anionic surfactants, nonionic surfactants, cationic surfactants and amphoteric surfactants can be used.

Specific examples of the anionic surfactant include fatty acid salts such as mixed fatty acid sodium soap, semi-hardened milk fatty acid sodium soap, sodium stearate soap, potassium oleate soap, castor oil potassium soap or the like; alkylsulfuric acid ester salts such as sodium dodecylsulfate, higher alcohol sodium sulfate, sodium laurylsulfate and triethanolamine laurylsulfate; alkylbenzenesulfonic acid salts such as sodium dodecylbenzenesulfonate; alkyl naphthalenesulfonic acid salts such as sodium alkylnaphthalenesulfonate; alkylsulfosuccinate salts such as sodium dialkylsulfosuccinate; alkyl diphenyl ether disulfonate salts such as sodium alkyl diphenyl ether disulfonate; alkyl phosphates such as potassium alkyl phosphate; polyoxyethylene alkyl (or alkylallyl) sulfuric acid ester salts such as polyoxyethylene lauryl ether sodium sulfate, polyoxyethylene alkyl ether sodium sulfate, triethanolamine polyoxyethylene alkyl ether sulfate, sodium polyoxyethylene alkyl phenyl ether sulfate or the like; special reactive anionic surfactants; special carboxylic acid type surfactant; naphthalenesulfonic acid-formaldehyde condensate such as sodium salt of β-naphthalenesulfonic acid-formaldehyde condensate, sodium salt of special aromatic sulfonic acid-formaldehyde condensate or the like; special polycarboxylic acid-based polymer surfactant; polyoxyethylene alkyl phosphates, and the like. As specific examples of the nonionic surfactant include polyoxyethylene alkyl ethers such as polyoxyethylene lauryl ether, polyoxyethylene cetyl ether, polyoxyethylene stearyl ether, polyoxyethylene oleyl ether, polyoxyethylene higher alcohol ether or the like; polyoxyethylene alkyl aryl ethers such as polyoxyethylene nonylphenyl ether; polyoxyethylene derivatives; sorbitan fatty acid esters such as sorbitan monolaurate, sorbitan monopalmitate, sorbitan monostearate, sorbitan tristearate, sorbitan monooleate, sorbitan trioleate, sorbitan sesquioleate, sorbitan distearate or the like; polyoxyethylene sorbitan fatty acid esters such as polyoxyethylene sorbitan monolaurate, polyoxyethylene sorbitan monolaurate, polyoxyethylene sorbitan monopalmitate, polyoxyethylene sorbitan monostearate, polyoxyethylene sorbitan tristearate, polyoxyethylene sorbitan monooleate, polyoxyethylene sorbitan trioleate, or the like; polyoxyethylene sorbitol fatty acid ester such as tetraoleic acid polyoxyethylene sorbitol; glycerin fatty acid esters such as glycerol monostearate, glycerol monooleate, self-emulsifying glycerol monostearate, or the like; polyoxyethylene fatty acid esters such as polyethylene glycol monolaurate, polyethylene glycol monostearate, polyethylene glycol distearate, polyethylene glycol monooleate, or the like; polyoxyethylene alkylamine;

polyoxyethylene hardened castor oil; alkyl alkanolamides, and the like. As specific examples of the cationic surfactant and the amphoteric surfactant include alkylamine salts such as coconut amine acetate,
stearylamine acetate, or the like; quaternary ammonium salts such as lauryl trimethyl ammonium chloride, stearyl trimethyl ammonium chloride, cetyltrimethylammonium chloride, distearyldimethylammonium chloride, alkylbenzyldimethylammonium chloride, or the like; alkyl betaine such as lauryl betaine, stearyl betaine.
lauryl carboxymethyl hydroxyethyl imidazolinium betaine, or the like; amine oxide such as lauryl dimethylamine oxide, and the like.

The surfactant may be used in an amount of about 0.001 to 0.1% by weight based on the monomer mixture, which can induce a stable bubble generation of the foaming agent and induce so that the bubbles are stably dispersed in the monomer mixture for a long period of time.

The monomer mixture may further include additives such as a thickener, a plasticizer, a preservation stabilizer, an antioxidant, etc., if necessary.

The raw materials such as the water-soluble ethylenically unsaturated monomer, the polymerization initiator, the internal crosslinking agent and the additives may be prepared in the form of the monomer mixture solution which is dissolved in a solvent.

The solvent that can be used is not limited by its constitution as long as it can dissolve the above-described components. For example, one or more solvents selected from the group consisting of water, ethanol, ethyleneglycol, diethyleneglycol, triethyleneglycol, 1,4-butanediol, propyleneglycol, ethyleneglycol monobutylether, propyleneglycol monomethylether, propyleneglycol monomethylether acetate, methylethylketone, acetone, methylamylketone, cyclohexanone, cyclopentanone, diethyleneglycol monomethylether, diethyleneglycol ethylether, toluene, xylene, butylolactone, carbitol, methylcellosolve acetate, and N,N-dimethyl acetamide, and so on may be used alone or in combination with each other.

The solvent may be included in a residual amount of excluding the above-described components from the total weight of the monomer mixture.

Meanwhile, the method for forming a hydrogel polymer by the thermal polymerization or photopolymerization of such a monomer composition is not particularly limited by its constitution as long as it is a polymerization method commonly used in the art.

Specifically, the polymerization process may be largely classified into a thermal polymerization and a photo-polymerization depending on a polymerization energy source. Usually, in the case of the thermal polymerization, it may be carried out in a reactor like a kneader equipped with stirring spindles. At this time, the polymerization temperature of the monomer mixture can be adjusted to about 30 to 110° C. to form a hydrogel polymer having an appropriate crosslinking structure. Means for achieving the polymerization temperature within the above-described range is not particularly limited, and the heating can be carried out by providing a heating medium or directly providing a heating source. The type of heat medium that can be used here includes a heated fluid such as steam, hot air, hot oil, etc., but it is not limited thereto. Further, the temperature of the heating medium to be provided can be appropriately selected in consideration of the means of the heating medium, the temperature raising speed, and the temperature raising target temperature. Meanwhile, as a heat source to be provided directly, there may be mentioned a heating method using electricity or a heating method using gas, but is not limited to the above example.

Meanwhile, in the case of the photo-polymerization, it may be carried out in a reactor equipped with a movable conveyor belt. However, the above-described polymerization method is an example only, and the present invention is not limited thereto.

For example, when the thermal polymerization is carried out by providing hot air to a reactor like a kneader equipped with the agitating spindles, or heating the reactor, the hydrogel polymer discharged from the outlet of the reactor can be obtained. The hydrogel polymer thus obtained can be in the form of several centimeters or several millimeters depending on the type of agitating spindles equipped in the reactor. Specifically, the size of the obtained hydrogel polymer may vary depending on the concentration of the monomer mixture to be injected thereto, the injection speed, or the like.

Further, as described above, when the photo-polymerization is carried out in a reactor equipped with a movable conveyor belt, the obtained hydrogel polymer may be usually a sheet-like hydrogel polymer having a width of the belt. In this case, the thickness of the polymer sheet may vary depending on the concentration of the monomer mixture to be injected thereto and the injection speed, but usually, it is preferable to supply the monomer mixture so that a sheet-like polymer having a thickness of about 0.5 to about 10 cm can be obtained. If the monomer mixture is supplied to such an extent that the thickness of the sheet-like polymer is too thin, it is undesirable because the production efficiency is low, and if the thickness of the sheet-like polymer is more than 10 cm, the polymerization reaction cannot be uniformly carried out over the entire thickness.

The polymerization time of the monomer mixture is not particularly limited, and can be adjusted to about 30 seconds to 60 minutes.

The hydrogel polymer obtained by the above-mentioned method may have a water content of about 30 to about 80% by weight. Meanwhile, the "water content" as used herein means a weight occupied by moisture with respect to a total amount of the hydrogel polymer, which may be the value obtained by subtracting the weight of the dried polymer from the weight of the hydrogel polymer. Specifically, the water content can be defined as a value calculated by measuring the weight loss due to evaporation of moisture in the polymer in the process of drying by raising the temperature of the polymer through infrared heating. At this time, the water content is measured under the drying conditions determined as follows: the drying temperature is increased from room temperature to about 180° C. and then the temperature is maintained at 180° C., and the total drying time is set to 40 minutes, including 5 minutes for the temperature rising step.

After the monomers are polymerized into cross-linked polymer, the base polymer powder can be obtained through steps such as drying, pulverization, classification, and the like, and through the steps such as pulverization and classification, the base polymer powder and the super absorbent polymer obtained therefrom are suitably produced and provided so as to have a particle diameter of about 150 to 850 μm. More specifically, at least about 95% by weight or more of the base polymer powder and the super absorbent polymer obtained therefrom has a particle diameter of about 150 μm to 850 μm and a fine powder having a particle diameter of less than about 150 μm can contained in an amount of less than about 3% by weight.

As described above, as the particle diameter distribution of the base polymer powder and the super absorbent polymer is adjusted to the preferable range, the super absorbent polymer finally produced can exhibit excellent absorbent properties.

On the other hand, the method of drying, pulverization and classification will be described in more detail below.

First, when drying the hydrogel polymer, a coarsely pulverizing step may be further carried out before drying in order to increase the efficiency of the drying step, if necessary.

A pulverizing machine is not limited by its configuration, and specifically, it may include any one selected from the group consisting of a vertical pulverizer, a turbo cutter, a turbo grinder, a rotary cutter mill, a cutter mill, a disc mill, a shred crusher, a crusher, a chopper, and a disc cutter. However, it is not limited to the above-described examples.

In this case, the coarsely pulverizing step may be carried out so that the particle diameter of the hydrogel polymer becomes about 0.2 mm to about 15 mm.

Pulverizing the hydrogel polymer into a particle diameter of less than 0.2 mm is technically not easy due to its high moisture content, and agglomeration phenomenon between the pulverized particles may occur. Meanwhile, if the polymer is pulverized into a particle diameter of greater than 15 mm, the effect of increasing the efficiency in the subsequent drying step may be insignificant.

The hydrogel polymer coarsely pulverized as above or the hydrogel polymer immediately after polymerization without the coarsely pulverizing step is subjected to a drying step. In this case, the drying temperature of the drying step may be about 50° C. to about 250° C.

When the drying temperature is less than 50° C., it is likely that the drying time becomes too long or the physical properties of the super absorbent polymer finally formed is deteriorated, and when the drying temperature is higher than 250° C., only the surface of the polymer is excessively dried, and thus it is likely that fine powder is generated during the subsequent pulverizing step, and the physical properties of the super absorbent polymer finally formed is deteriorated.

Meanwhile, the drying time may be about 20 minutes to about 15 hours, in consideration of the process efficiency and the like, but it is not limited thereto.

In the drying step, the drying method may also be selected and used without being limited by its constitution if it is a method generally used for drying the hydrogel polymer. Specifically, the drying step may be carried out by a method such as hot air supply, infrared irradiation, microwave irradiation or ultraviolet irradiation. After the drying step as above is carried out, the moisture content of the polymer may be about 0.1% to about 10% by weight.

Subsequently, the dried polymer obtained through the drying step is subjected to a pulverization step.

The polymer powder obtained through the pulverizing step may have a particle diameter of about 150 μm to about 850 μm. Specific examples of a pulverizing device that can be used to achieve the above particle diameter may include a pin mill, a hammer mill, a screw mill, a roll mill, a disc mill, a jog mill or the like, but the present invention is not limited thereto.

Also, in order to control the physical properties of the super absorbent polymer powder finally commercialized after the pulverization step, a separate step of classifying the polymer powder obtained after the pulverization depending on the particle diameter may be undergone. Preferably, a polymer having a particle diameter of about 150 μm to about 850 μm is classified and only the polymer powder having such a particle diameter is subjected to the surface crosslinking reaction and finally commercialized. Since the particle diameter distribution of the base polymer powder obtained through such a process has already been described above, a further detailed description thereof will be omitted.

On the other hand, after the step of forming the base polymer powder described above, the surface of the base polymer powder can be subjected a double crosslinking to form the first and second surface cross-linked layers, whereby a super absorbent polymer having GBP change ratio of 0.90 or less can be provided.

Specifically, in the step of forming the surface cross-linked layer, the surface of the base polymer powder can be further subjected to a first crosslinking using an epoxy-based surface crosslinking agent. Consequently, a first surface cross-linked layer containing a cross-linked structure derived from an epoxy-based surface crosslinking agent is formed on the base polymer powder.

In this case, as the surface crosslinking agent, polyglycidyl ether may be used. More specifically, at least one selected from the group consisting of ethylene glycol diglycidyl ether, propylene glycol diglycidyl ether, butanediol diglycidyl ether, hexanediol diglycidyl ether, diethyleneglycol diglycidyl ether, triethylene glycol diglycidyl ether, polyethylene glycol diglycidyl ether, dipropylene glycol diglycidyl ether, tripropylene glycol diglycidyl ether, polypropylene glycol diglycidyl ether and glycerol triglycidyl ether may be used.

Such an epoxy-based surface crosslinking agent may be used in an amount of about 0.01 to 3% by weight based on the total weight of the base polymer powder. It is possible to provide a super absorbent polymer exhibiting excellent physical properties even after being swollen by adjusting the content range of the epoxy-based surface crosslinking agent within the above-mentioned range.

In the first surface crosslinking step, the first surface crosslinking reaction can be carried out by further adding one or more inorganic materials selected from the group consisting of silica, clay, alumina, silica-alumina composite material, titania, zinc oxide and aluminum sulfate in addition to the epoxy-based surface crosslinking agent. The inorganic material can be used in the form of powder or liquid, and in particular, it can be used as alumina powder, silica-alumina powder, titania powder or nanosilica solution. In addition, the inorganic material can be used in an amount of about 0.05% to about 2% by weight based on the total weight of the base polymer powder.

Moreover, in the first surface crosslinking step, as the surface crosslinking proceeds by adding a polyvalent metal cation in place of the inorganic material or together with the inorganic material, the surface crosslinking structure of the super absorbent polymer can be further optimized. This is presumably because such a metal cation can further reduce the crosslinking distance by forming a chelate with the carboxyl group (COOH) of the super absorbent polymer.

The method of adding the surface crosslinking agent, and optionally an inorganic substance and/or a polyvalent metal cation to the base polymer powder are not limited by its constitution. For example, a method of adding surface crosslinking agent and a base polymer powder to a reaction tank and mixing them, or a method of spraying a surface crosslinking agent or the like to the base polymer powder, or a method of adding a base polymer powder and a surface crosslinking agent to a continuously operated mixer and mixing them, or the like, may be used.

When the surface crosslinking agent is added, water and methanol can be additionally mixed together and added. When water and methanol are added, there is an advantage that the surface crosslinking agent can be uniformly dispersed in the base polymer powder. At this time, the amount of water and methanol added can be appropriately adjusted in order to induce a more uniform dispersion of the epoxy-based crosslinking agent, prevent the aggregation phenomenon of the polymer powders, and further optimize the depth of penetration of the epoxy-based surface crosslinking agent.

The first surface crosslinking reaction may be performed by heating the base polymer powder to which the epoxy-based surface crosslinking agent is added at a temperature of about 120° C. to 160° C. about 130° C. to 150° C. or about 140° C. for about 5 to 40 minutes, about 10 to 30 minutes or about 20 minutes. In particular, in order to produce a super absorbent polymer that more suitably fulfills physical properties according to one embodiment, the conditions of the first surface crosslinking step can adjust the maximum reaction temperature to about 120° C. to 160° C. The retention time at the maximum reaction temperature can be adjusted under the conditions of about 5 to 40 minutes, or about 10 to 30 minutes or about 20 minutes. In addition, from a temperature at the beginning of the first reaction, for example, a temperature of about 80° C. or more, the temperature raising time until reaching the maximum reaction temperature can be controlled to be about 10 minutes or more, or about 10 minutes or more and 1 hour or less.

Meanwhile, in the step of forming the surface cross-linked layer, the surface of the first surface cross-linked powder obtained through the first surface cross-linking step is subjected to a second crosslinking using a non-epoxy based surface crosslinking agent. Consequently, a first surface cross-linked layer containing a crosslinking structure derived from an epoxy-based surface crosslinking agent and a second surface cross-linked layer containing a crosslinking structure derived from a non-epoxy based surface crosslinking agent are formed on the base polymer powder.

In the step of forming the surface cross-linked layer, as the first surface crosslinking step using an epoxy based surface crosslinking agent and the second surface crosslinking step using a non-epoxy based surface crosslinking agent are sequentially performed, the second surface crosslinking layer may be formed on the first surface crosslinking layer.

Due to such double surface crosslinking step, it is possible to provide a super absorbent polymer having a small GBP change ratio calculated by Formula 1.

As the non-epoxy based surface crosslinking agent, a polyol, a carbonate compound or a mixture thereof may be used. More specifically, the polyol may be at least one selected from the group consisting of ethylene glycol, propylene glycol, 1,4-butanediol, 1,6-hexanediol, 1,2-hexanediol, 1,3-hexanediol, 2-methyl-1,3-propanediol, 2,5-hexanediol, 2-methyl-1,3-pentanediol, 2-methyl-2,4-pentanediol, tripropylene glycol, and glycerol. The carbonate-based compound may be at least one selected from the group consisting of ethylene carbonate and propylene carbonate. Among them, a carbonate-based compound can be used to exhibit more excellent gel strength at the time of swelling.

Such non-epoxy based surface crosslinking agent may be used in an amount of about 0.1 to 3% by weight based on the total weight of the first surface cross-linked powder. It is possible to provide a super absorbent polymer exhibiting excellent physical properties even after being swollen by adjusting the content range of the non-epoxy based surface crosslinking agent within the above range.

In the second surface crosslinking step, an inorganic material, a polyvalent metal cation, water, methanol and the like can be further used together with the non-epoxy based surface cross linking agent, similarly to the first surface crosslinking step. As described in the first surface crosslinking step, a non-epoxy based surface crosslinking agent may be added to the first surface cross-linked powder. Specific details related thereto have been described above, and so they are omitted here.

The second surface crosslinking reaction may be performed by heating the first surface cross-linked powder to which the non-epoxy based surface crosslinking agent is added at a temperature of about 170° C. to 210° C., about 180° C. to 200° C. or about 190° C. for about 5 to 40 minutes, about 10 to 30 minutes or about 20 minutes. In particular, in order to produce a super absorbent polymer that more suitably fulfills physical properties according to one embodiment, the conditions of the second surface crosslinking step can adjust the maximum reaction temperature to about 170° C. to 210° C. The retention time at the maximum reaction temperature can be adjusted under the conditions of about 5 to 40 minutes, or about 10 to 30 minutes or about 20 minutes. In addition, from a temperature at the beginning of the first reaction, for example, a temperature of about 80° C. or more, the temperature raising time until reaching the maximum reaction temperature can be controlled to be about 10 minutes or more, or about 10 minutes or more and 1 hour or less.

The temperature raising means for the first and second surface crosslinking reactions is not particularly limited. The heating can be carried out by providing a heating medium or directly providing a heating source. The type of heat medium that can be used here includes a heated fluid such as steam, hot air, hot oil, etc., but it is not limited thereto. Further, the temperature of the heating medium to be provided can be appropriately selected in consideration of the means of the heating medium, the temperature raising speed, and the temperature raising target temperature. Meanwhile, a heat source to be provided directly may include a heating method using electricity or a heating method using gas, but is not limited thereto.

Meanwhile, according to another embodiment of the present invention, there is provided a super absorbent polymer; comprising: a base polymer powder including a cross-linked polymer in which a water-soluble ethylenically unsaturated monomer having at least partially neutralized acidic groups is cross-linked in the presence of an internal crosslinking agent; and first and second surface cross-linked layers that are further cross-linked from the cross-linked polymer in the presence of a surface crosslinking agent and are formed on the base polymer powder, wherein the first and second surface cross-linked layers each include a cross-linked structure derived from surface crosslinking agents that are different from each other; and having an absorbency under load (AUL) under 0.9 psi for a physiological saline solution is 19 to 25 g/g, and a GBP change ratio calculated by the following Formula 1 is 0.90 or less.

$$\frac{0.3\ GBP - 0.3\ AGBP}{0.3\ GBP}$$ [Formula 1]

in Formula 1, 0.3 GBP is a gel bed permeability (GBP) under 0.3 psi for a 0.9 wt % sodium chloride aqueous solution of a super absorbent polymer, 0.3 AGBP is a gel bed permeability (GBP) under 0.3 psi for a physiological saline solution of a super absorbent polymer having a particle size from 300 to 600 μm after swelling and drying which is obtained by a process of adding 5 g of the super absorbent polymer to 125 g of distilled water, stirring the resultant for 1 minute, drying the swollen super absorbent polymer at 100° C. for 3 hours, and then classifying the dried polymer through a U.S. standard 30 mesh screen and a U.S. standard 50 mesh screen.

In the super absorbent polymer according to another embodiment of the present invention, the first and second surface cross-linked layers include a cross-linked structure derived from surface crosslinking agents that are different from each other, and the AUL satisfies 19 to 25 g/g, and thus the above-mentioned effects can be exhibited, even if the first and second surface cross-linked layers do not include the cross-linked structure derived from epoxy-based and non-epoxy-based surface crosslinking agents, as in the super absorbent polymer according to one embodiment. Therefore, the super absorbent polymer according to another embodiment can be produced as described above except for the above limitations.

Hereinafter, the function and effect of the present invention will be described in more detail by way of specific examples. It is to be understood, however, that these examples are provided for illustrative purposes only and the scope of the invention is not limited in any way.

Example 1: Preparation of Super Absorbent Polymer

To a glass reactor were added 500 g of acrylic acid, 39 g of polyethylene glycol diacrylate (PEGDA, weight average molecular weight: 400), 2.1 g of allyl methacrylate and 20 g of IRGACURE 819. Then, 809.5 g of a 24 wt % caustic soda solution was slowly added dropwise to the glass reactor.

It was waited that, during dropwise addition of the caustic soda solution, the temperature of the mixed solution was increased to about 72° C. or higher due to neutralization heat, and then the mixed solution was cooled. The degree of neutralization of acrylic acid in the mixed solution thus obtained was about 70 mol %.

When the temperature of the mixed solution was cooled to about 45° C. 2.14 g of sodium bicarbonate and 0.27 g of sodium dodecyl sulfate were added to the mixed solution, and light was irradiated for 1 minute to perform light polymerization.

Then, the polymer obtained through the polymerization reaction was passed through a hole having a diameter of 11 mm using a meat chopper to produce a crump.

Then, the crumps were dried in an oven capable of shifting airflow upward and downward. The crumps were uniformly dried by flowing hot air at 180° C. from the bottom to the top for 15 minutes and again from the top to the bottom for 15 minutes, so that a water content of the dried crump became 2% or less.

The dried crump was pulverized using a pulverizing device and classified to obtain a base polymer having a size of 150 to 850 μm.

On the other hand, 0.04 g of ethylene glycol diglycidyl ether (DENACOL EX 810), 3 g of water and 3 g of methanol were mixed to prepare a first surface cross-linked solution, 0.2 g of ethylene carbonate, 3 g of water and 3 g of methanol to prepare a second surface crosslinking liquid.

Subsequently, the first surface crosslinking liquid was sprayed onto 100 g of the prepared base polymer powder and mixed with stirring at room temperature so that the first surface crosslinking liquid was evenly distributed on the base polymer powder. Then, the base polymer powder mixed with the first surface crosslinking liquid was added to the surface cross-linking reactor and the surface crosslinking reaction proceeded. In the surface crosslinking reactor, it was confirmed that the base polymer powder was gradually heated at an initial temperature near 80° C. Then, the surface crosslinking reactor was operated so as to reach the maximum reaction temperature of 140° C. after 30 minutes from the initial temperature. After reaching the maximum reaction temperature, additional reaction was carried out for 20 minutes to obtain a first surface cross-linked powder.

Then, the second surface crosslinking liquid was sprayed onto the first surface crosslinking powder and mixed with stirring at room temperature so that the second surface crosslinking liquid was distributed evenly on the first surface cross-linked powder. Then, the first surface cross-linked powder mixed with the second surface crosslinking liquid was added to the surface crosslinking reactor, and the surface crosslinking reaction proceeded. In the surface crosslinking reactor, it was confirmed that the first surface cross-linked powder was gradually heated at an initial temperature near 80° C. Then, the surface crosslinking reactor was operated so as to reach the maximum reaction temperature of 190° C. after 30 minutes from the initial temperature. After reaching the maximum reaction temperature, additional reaction was carried out for 20 minutes to obtain a second surface cross-linked powder. Then, such super absorbent polymer was pulverized and classified into a standard mesh according to ASTM standard to obtain a super absorbent polymer having a particle diameter of 150 to 850 µm.

Example 2: Production of Super Absorbent Polymer

A surface cross-linked super absorbent polymer was produced in the same manner as in Example 1, except that a solution prepared by mixing 1 g of ethylene carbonate and 4.3 g of water was used as the second surface crosslinking liquid in Example 1.

Example 3: Production of Super Absorbent Polymer

A surface cross-linked super absorbent polymer was produced in the same manner as in Example 1, except that a solution prepared by mixing 1 g of propylene carbonate and 4.3 g of water was used as the second surface crosslinking liquid in Example 1.

Example 4: Production of Super Absorbent Polymer

A surface cross-linked super absorbent polymer was produced in the same manner as in Example 1, except that a solution prepared by mixing 1 g of ethylene carbonate, 1 g of propylene carbonate and 4.3 g of water was used as the second surface crosslinking liquid in Example 1.

Example 5: Production of Super Absorbent Polymer

A surface cross-linked super absorbent polymer was produced in the same manner as in Example 1, except that a solution prepared by mixing 0.4 g of ethylene carbonate, 3 g of water and 3 g of methanol was used as the second surface crosslinking liquid in Example 1.

Comparative Example 1: Production of Super Absorbent Polymer

A surface cross-linked super absorbent polymer was produced in the same manner as in Example 1, except that 0.04 g of ethylene carbonate, 3 g of water and 3 g of methanol were used as the first surface crosslinking liquid, and 0.2 g of glycerol, 3 g of water and 3 g of methanol were used as a second surface crosslinking liquid in Example 1.

Comparative Example 2: Production of Super Absorbent Polymer

A surface cross-linked super absorbent polymer was produced in the same manner as in Example 1, except that a solution prepared by mixing 0.04 g of ethylene glycol diacrylate, 3 g of water and 3 g of methanol was used as the first surface crosslinking liquid in Example 1.

Comparative Example 3: Production of Super Absorbent Polymer

A surface cross-linked super absorbent polymer was produced in the same manner as in Example 1, except that the surface of the base polymer powder was cross-linked once under the condition of the second surface crosslinking step, by using a solution prepared by mixing 0.04 g of ethylene glycol diglycidyl ether (DENACOL EX 810), 0.5 g of ethylene glycol, 3 g of water and 3 g of methanol, instead of the first and second surface crosslinking liquids in Example 1.

Comparative Example 4: Production of Super Absorbent Polymer

A surface cross-linked super absorbent polymer was produced in the same manner as in Example 1, except that the second surface crosslinking was performed without spraying the second surface crosslinking liquid onto the first surface cross-linked powder in Example 1.

Comparative Example 5: Production of Super Absorbent Polymer

A surface cross-linked super absorbent polymer was produced in the same manner as in Example 1, except that the first crosslinking was performed by spraying the second surface crosslinking liquid at the spraying time point of the first surface crosslinking liquid, and then the second surface crosslinking was performed without further spraying the second surface crosslinking liquid at the spraying time point of the first surface cross-linking liquid.

Test Example 1: Evaluation of Properties of Super Absorbent Resin

Properties of the super absorbent polymer produced according to Examples and Comparative Examples were evaluated by the following method, and the results are shown in Table 1 below.

(1) Centrifuge Retention Capacity (CRC)

The centrifuge retention capacity (CRC) for a physiological saline solution was measured for each super absorbent polymer produced according to Examples and Comparative Examples according to EDANA recommended test method No. WSP 241.2.

Specifically, a super absorbent polymer having a particle diameter of 150 to 850 Lm which was passed through a U.S. standard 20 mesh screen and retained on a U.S. standard 100 mesh screen was prepared from a super absorbent polymer for measuring the centrifuge retention capacity.

Then, the super absorbent polymer $W_0$ (g, about 0.2 g) having a particle diameter of 150 to 850 Lm was uniformly placed into a nonwoven fabric-made bag, followed by sealing. Then, the bag was immersed in 0.9% by weight of physiological saline solution at room temperature. After 30 minutes, the bag was dehydrated at 250 G for 3 minutes with a centrifuge, and the weight $W_2$ (g) of the bag was then measured. Meanwhile, after carrying out the same procedure using an empty bag not containing a super absorbent polymer, the resultant weight $W_1$ (g) was measured.

Using the respective weights thus obtained, a centrifuge retention capacity was confirmed according to the following Calculation Formula 1:

$$\text{CRC (g/g)} = \{[W_2 \text{ (g)} - W_1 \text{ (g)}]/W_0 \text{ (g)}\} - 1 \qquad \text{[Calculation Formula 1]}$$

in Calculation Formula 1, $W_0$ (g) is an initial weight (g) of the sample having a particle diameter of 150 to 850 μm, $W_1$ (g) is a weight of a nonwoven fabric-made empty bag not containing the sample, measured after immersing the nonwoven fabric-made empty bag in a physiological saline solution for 30 minutes and then dehydrating the same by using a centrifuge at 250 G for 3 minutes, and $W_2$ (g) is a weight of the nonwoven fabric-made bag including a sample, measured after soaking and absorbing the nonwoven fabric-made bag in a physiological saline solution at room temperature for 30 minutes, and then dehydrating the same by using a centrifuge at 250 G for 3 minutes.

(2) Absorbency Under Load (AUL)

The absorbency under load (AUL) at 0.9 psi for a physiological saline solution of the super absorbent polymer was measured according to EDANA recommended test method No. WSP 242.2.

Specifically, a 400 mesh stainless steel net was installed in the bottom of a plastic cylinder having an inner diameter of 25 mm. $W_0$ (g, 0.16 g) of a super absorbent polymer for measuring the absorbency under load were uniformly scattered on the screen under conditions of room temperature and relative humidity of 50%. Then, a piston which could provide a load of 6.3 kPa (0.9 psi) uniformly was put thereon. At this time, the piston used was designed so that the outer diameter was slightly smaller than 25 mm and thus it could move freely up and down without any gap with the inner wall of the cylinder. Then, the weight $W_3$ (g) of the device prepared in this way was measured.

After putting a glass filter having a diameter of 90 mm and a thickness of 5 mm in a Petri dish having the diameter of 150 mm, 0.90% by weight of a sodium chloride aqueous solution (physiological saline solution) was poured in the Petri dish. At this time, the physiological saline solution was poured until the surface level became equal to the upper surface of the glass filter. Then, a sheet of filter paper having a diameter of 90 mm was put on the glass filter.

Subsequently, the prepared device was placed on the filter paper so that the super absorbent polymer in the device was swelled by a physiological saline solution under load. After one hour, the weight $W_4$ (g) of the device containing the swollen super absorbent polymer was measured.

Using the weight thus measured, the absorbency under load was calculated according to the following Calculation Equation 2.

$$\text{AUL (g/g)} = [W_4 \text{ (g)} - W_3 \text{ (g)}]/W_0 \text{ (g)} \qquad \text{[Calculation Formula 2]}$$

in Calculation Equation 2, $W_0$ (g) is an initial weight (g) of the super absorbent polymer, $W_3$ (g) is the total sum of a weight of the super absorbent polymer and a weight of the device capable of providing a load to the super absorbent polymer, and $W_4$ (g) is the total sum of a weight of the super absorbent polymer and a weight of the device capable of providing a load to the super absorbent polymer, after absorbing a physiological saline solution to the super absorbent polymer under a load (0.9 psi) for 1 hour.

(3) Gel Bed Permeability (GBP)

The gel bed permeability (GBP) for a physiological saline solution of the super absorbent polymer was measured according to the following method described in Korean Patent Application No. 10-2014-7018005.

Specifically, the apparatus shown in FIGS. 1 to 3 was used to measure the free swell GBP. First, the plunger 536 installed with the weight 548 was placed in an empty sample container 530, and the height from the top of the weight 548 to the bottom of the sample container 530 was measured to an accuracy of 0.01 mm using an appropriate gauge. The force to which the thickness gauge applied during the measurement was adjusted to less than about 0.74 N.

Meanwhile, a super absorbent polymer having a particle diameter of 300 to 600 μm was obtained by selectively classifying a super absorbent polymer which was passed through a US standard 30 mesh screen and retained on a US standard 50 mesh screen.

About 2.0 g of the super absorbent polymer classified in this way was placed in the sample container 530 and spread out evenly on the bottom of the sample container. Then, the container not containing the plunger 536 and the weight 548 therein, was submerged in a 0.9 wt % sodium chloride aqueous solution (physiological saline solution) for about 60 minutes and allowed the super absorbent polymer to swell under no load condition. At this time, the sample container 530 was placed on the mesh located in a liquid reservoir so that the sample container 530 was raised slightly above the bottom of the liquid reservoir. As the mesh, those which did not affect the movement of the physiological saline solution into the sample container 530 were used. During saturation, the height of the physiological saline solution could be adjusted such that the surface within the sample container was defined by the swollen super absorbent polymer, rather than the physiological saline solution.

At the end of this period, the assembly of the plunger 536 and weight 548 was placed on the swollen super absorbent polymer 568 in the sample container 530 and then the sample container 530, plunger 536, weight 548 and swollen super absorbent polymer 568 were removed from the solution. Thereafter, before GBP measurement, the sample container 530, plunger 536, weight 548 and swollen super absorbent polymer 568 were placed on a flat, large grid non-deformable plate of uniform thickness for about 30 seconds. The height from the top of the weight 548 to the bottom of the sample container 530 was measured again by using the same thickness gauge as previously used. Then, the height measurement value of the device in which the plunger 536 equipped with the weight 548 was placed in the empty sample container 530 was subtracted from the height measurement value of the device including the swollen super absorbent polymer 568, thereby obtaining the thickness or height "H" of the swollen super absorbent polymer.

For the GBP measurement, 0.9 wt % physiological saline solution was flowed into the sample container 530 containing the swollen super absorbent polymer 568, the plunger 536 and the weight 548. The flow rate of a physiological saline solution into the container was adjusted to cause the physiological saline solution to overflow the top of the cylinder 534, thereby resulting in a consistent head pressure equal to the height of the sample container 530. Then, the quantity of solution passing through the swollen super absorbent polymer 568 versus time was measured gravimetrically using the scale 602 and beaker 603. Data points from the scale 602 were collected every second for at least sixty seconds once the overflow has started. The flow rate (Q) passing through the swollen super absorbent polymer 568 was determined in units of grams/second (g/s) by a linear least-square fit of fluid passing through the sample 568 (in grams) versus time (in seconds).

Using the data thus obtained, the GBP (cm$^2$) was calculated according to the following Calculation Equation 3.

$$K=[Q*H*\mu]/[A*\rho*P] \qquad \text{[Calculation Equation 3]}$$

in Calculation Equation 3,
K is a gel bed permeability (cm$^2$),
Q is a flow rate (g/sec)
H is a height of swollen super absorbent polymer (cm),
μ is a liquid viscosity (poise) (about 1 cP for the test solution used with this Test),
A is a cross-sectional area for liquid flow (28.27 cm$^2$ for the sample container used with this Test),
ρ is a liquid density (g/cm$^2$)(about 1 g/cm$^2$, for the physiological saline solution used with this Test), and
P is a hydrostatic pressure (dynes/cm$^2$) (normally about 7,797 dyne/cm$^2$).

The hydrostatic pressure was calculated from the equation P=ρ*g*h, where ρ is a liquid density (g/cm$^2$), g is a gravitational acceleration (nominally 981 cm/sec$^2$), and h is a fluid height (for example, 7.95 cm for the GBP Test described herein)

At least two samples were tested and the results were averaged to determine the free swell GBP of the super absorbent polymer, and the unit was converted to darcy (1 darcy=0.98692×10$^{-8}$ cm$^2$).

(4) Gel Bed Permeability at 0.3 Psi (0.3 GBP)

The initial gel bed permeability (GBP) under 0.3 psi (0.3 GBP) of the super absorbent polymers produced according to Examples and Comparative Examples, and the gel bed permeability (GBP) under 0.3 psi (0.3 AGBP) measured after swelling the super absorbent polymer with distilled water and then drying the swollen polymer were measured, and the GBP change ratio was calculated according to the following Formula 1. The results are shown in Table 1 below.

$$\frac{0.3\ GBP - 0.3\ AGBP}{0.3\ GBP} \qquad \text{[Formula 1]}$$

Specifically, 5 g of the super absorbent polymer was added to 125 g of distilled water and stirred for 1 minute to swell the super absorbent resin. Then, the swollen super absorbent polymer was taken out and spread out evenly on a mesh screen to prevent the polymer from sticking, and then dried in an oven at 100° C. for 3 hours.

In order to measure the gel bed permeability at 0.3 psi of the super absorbent polymer after swelling and drying, a super absorbent polymer passed through a US standard 30 mesh screen and retained on a US standard 50 mesh screen was selectively classified to obtained a super absorbent polymer having a particle diameter of 300 to 600 μm.

Then, the gel bed permeability (GBP) under 0.3 psi (0.3 GBP) for a physiological saline solution of the super absorbent polymers produced according to Examples and Comparative Examples, and the super absorbent polymers swollen and dried according to the above description was measured.

Specifically, the gel bed permeability (GBP) under 0.3 psi was measured in the same manner as in (3) method of measuring the free swell gel bed permeability, except for that, in the above-mentioned (3) method of measuring the free swell gel bed permeability, about 2.0 g of the classified super absorbent polymer was placed in the sample container 530 and spread out evenly on the bottom of the sample container, the assembly of the plunger 536 and weight 548 was placed on the swollen super absorbent polymer in the sample container and then the sample container is submerged in the physiological saline solution for about 60 minutes and allow the super absorbent polymer to swell under load of 0.3 psi.

TABLE 1

|  | CRC [g/g] | AUL [g/g] | Free swell GBP [darcy] | 0.3 GBP [darcy] | 0.3 AGBP [darcy] | GBP change ratio |
|---|---|---|---|---|---|---|
| Example 1 | 31.1 | 20.5 | 62 | 2.5 | 0.3 | 0.88 |
| Example 2 | 31.4 | 20.0 | 66 | 1.9 | 0.4 | 0.79 |
| Example 3 | 30.9 | 20.6 | 65 | 3.5 | 0.7 | 0.80 |
| Example 4 | 30.0 | 21.0 | 55 | 5.0 | 0.9 | 0.82 |
| Example 5 | 31.8 | 19.3 | 56 | 4.5 | 0.8 | 0.82 |
| Comparative Example 1 | 30.6 | 19.5 | 45 | 3.5 | 0.0 | 1.00 |
| Comparative Example 2 | 29.0 | 20.7 | 47 | 4.2 | 0.2 | 0.95 |
| Comparative Example 3 | 30.0 | 20.4 | 35 | 5.0 | 0.2 | 0.96 |
| Comparative Example 4 | 30.9 | 20.5 | 48 | 3.0 | 0.1 | 0.97 |
| Comparative Example 5 | 31.5 | 19.3 | 40 | 0.5 | 0.0 | 1.00 |

Referring to Table 1, it was confirmed that the super absorbent polymers of Examples 1 to 5, in which the first surface crosslinking was performed with the epoxy-based surface crosslinking agent and then the second surface crosslinking was performed with the non-epoxy based surface crosslinking agent according to an embodiment of the present invention exhibited well-balanced properties of a centrifuge retention capacity, an absorbency under load and a liquid permeability.

Meanwhile, it was confirmed that the super absorbent polymers of Comparative Examples 1 and 2 in which an epoxy-based surface crosslinking agent was not used in the first surface crosslinking step, the super absorbent polymer of Comparative Examples 3 in which the surface crosslinking step was performed only once by using two types of surface crosslinking agents simultaneously, and the super absorbent polymers of Comparative Examples 4 and 5 in which the surface crosslinking step was performed twice by using one type of surface crosslinking agent, exhibited a high GBP change ratio and thus did not exhibit a balanced absorption performance.

Test Example 2: Evaluation of Properties of Diaper

In order to confirm that the rewetting properties is better as the GBP change ratio GBP is smaller, a diaper sample was prepared using the super absorbent polymers produced according to Examples 1 to 5 in which the GBP change ratio was low and Comparative Examples 4 and 5 in which the GBP change ratio was high, and their re-wetting properties were evaluated and the results are shown in Table 2 below.

(1) Production of Diaper Sample

The initial gel bed permeability (GBP) under 0.3 psi (0.3 GBP) of the super absorbent polymers produced according to Examples and Comparative The super absorbent polymers were classified so that particles having 600 to 850 μm (classified using US standard 20 and 30 mesh screen), about 300 to 600 μm (classified using US standard 30 and 50 mesh screen) and about 90 to 300 μm (classified using US standard 50 and 170 mesh screen) had a weight ratio of 10:70:20.

Using the super absorbent polymers thus classified, the core of the diaper was composed of 70% by weight of super absorbent polymer and 30% by weight of fluff, and an acquisition distribution layer (ADL) and an ADL (acquisition distribution layer) and a top cover were laminated was laminated on the top of the core.

(2) Rewetting Properties of Diaper

The rewetting properties of the diaper were evaluated according to the method developed by Kimberly-Clark, capable of confirming the rewetting properties under no load or under load.

Specifically, in order to evaluate the rewetting properties under load, 85 mL of 0.9 wt % sodium chloride aqueous solution (physiological saline solution) was injected into the diaper. After 15 minutes, the weight was placed on the diaper and 85 mL of physiological saline solution was injected again while applying a load of 0.42 psi. After 15 minutes, the weight placed on the diaper was temporarily removed, and then the paper was placed on the diaper, the weight was again placed on the paper, and the paper was interposed between the diaper and the weight. After 2 minutes, the amount of the salt water leaking out by paper from the diaper was measured, and the rewetting amount (g/g) was calculated by the Calculation Equation 4.

Rewetting Amount (g)=$W_6$ (g)−$W_5$ (g)     [Calculation Equation 4]

in Calculation Equation 4, $W_5$ (g) is an initial weight of the paper, $W_6$ (g) is a weight of the paper that has absorbed a liquid leaking out from the diaper under a load (0.42 psi) for 2 minutes after a physiological saline solution was injected into the diaper under no load and under load.

EXPLANATION OF SIGN

500: GBP measuring device
528: Test apparatus assembly
530: Sample container
534: Cylinder
534a: Region having an outer diameter of 66 mm
536: Plunger
538: Shift
540: O-ring
544, 554, 560: hole
548: Annular weight
548a: Thru-bore
550: Plunger head
562: Shaft hole
564: 100 mesh stainless steel cross screen
566: 400 mesh stainless steel cross screen
568: Sample
600: Weir
601: Collection device
602: Scale
603: Beaker
604: Gauge pump

The invention claimed is:

1. A super absorbent polymer, comprising:
a base polymer powder including a cross-linked polymer polymerized from a water-soluble ethylenically unsaturated monomer having at least partially neutralized acidic groups and cross-linked in the presence of an internal crosslinking agent; and
first and second surface cross-linked layers formed on the base polymer powder, the first and second surface cross-linked layers formed by further cross-linking the cross-linked polymer in the presence of a surface crosslinking agent,
wherein the first and second surface cross-linked layers each include a cross-linked structure derived from epoxy-based and non-epoxy-based surface crosslinking agents,
wherein the first surface cross-linked layer includes at least one polyvalent metal cation and optionally an inorganic material,
and
wherein the superabsorbent polymer having a GBP change ratio calculated by the following Formula 1 of 0.90 or less, $$\frac{0.3\ GBP - 0.3\ AGBP}{0.3\ GBP}$$     [Formula 1]

TABLE 2

|  | Example 1 | Example 2 | Example 3 | Example 4 | Example 5 | Comparative Example 4 | Comparative Example 5 |
|---|---|---|---|---|---|---|---|
| GBP change ratio | 0.88 | 0.79 | 0.80 | 0.82 | 0.82 | 0.97 | 1.00 |
| Rewetting amount [g] | 4.34 | 3.18 | 4.80 | 4.64 | 5.00 | 5.88 | 5.59 |

Referring to Table 2, it was confirmed that when the super absorbent polymers of Examples having a low GBP change ratio was used, more excellent rewetting properties were obtained compared with the case of using the super absorbent polymers of Comparative Examples having a high GBP change ratio.

in Formula 1,
0.3 GBP is a gel bed permeability (GBP) under 0.3 psi for a 0.9 wt % sodium chloride aqueous solution of the super absorbent polymer,
0.3 AGBP is a gel bed permeability (AGBP) under 0.3 psi for a physiological saline solution of the super absorbent polymer having a particle size from 300 to 600 μm after swelling and drying which is obtained by a process of adding 5 g of the super absorbent polymer to 125 g of distilled water, stirring the resultant for 1 minute, drying the swollen super absorbent polymer at 100° C. for 3 hours, and then classifying the dried polymer through a U.S. standard 30 mesh screen and a U.S. standard 50 mesh screen.

2. The super absorbent polymer of claim 1, wherein it has a centrifuge retention capacity for a physiological saline solution of 30 to 40 g/g.

3. The super absorbent polymer of claim 1, wherein it has an absorbency under load under 0.9 psi for a physiological saline solution of 19 to 25 g/g.

4. The super absorbent polymer of claim 1, wherein it has a free swell gel bed permeability for a physiological saline solution of about 50 darcy to about 100 darcy.

\* \* \* \* \*